United States Patent [19]

Riihimaki et al.

[11] Patent Number: 5,256,064
[45] Date of Patent: Oct. 26, 1993

[54] DENTAL PROSTHESIS PLACEMENT INSTRUMENT

[75] Inventors: Roy E. Riihimaki, Libertyville; James M. Kudla, Mount Prospect; Jacqueline Dzierzak, Oak Park, all of Ill.

[73] Assignee: Hu-Friedy Mfg. Co., Inc., Chicago, Ill.

[21] Appl. No.: 853,939

[22] Filed: Mar. 19, 1992

Related U.S. Application Data

[63] Continuation-in-part of Ser. No. 655,797, Feb. 14, 1991, abandoned.

[51] Int. Cl.⁵ ................................................. A61C 3/00
[52] U.S. Cl. ...................................... 433/141; 433/215
[58] Field of Search .................... 433/3, 141, 146, 163, 433/215, 219; 294/1.1

[56] References Cited

U.S. PATENT DOCUMENTS

| | | | |
|---|---|---|---|
| 4,073,530 | 2/1978 | Seidler | 294/19 R |
| 4,834,654 | 5/1989 | Nussbaum | 433/141 |
| 4,848,815 | 7/1989 | Molloy | 294/1.1 |
| 4,953,902 | 9/1990 | Brown | 294/1.1 |
| 4,993,949 | 2/1991 | Hill | 433/141 |
| 5,040,981 | 8/1991 | Oliva | 433/141 |

FOREIGN PATENT DOCUMENTS 0700745  3/1931  France ................... 433/141

Primary Examiner—Gene Mancene
Assistant Examiner—Cindy A. Cherichetti
Attorney, Agent, or Firm—Dressler, Goldsmith, Shore, Sutker & Milnamow, Ltd.

[57] ABSTRACT

An instrument employing multiple adhesives for manipulating and placing dental prosthetics includes an autoclavable handpiece and a removable, disposable foam double-stick pad with pressure-sensitive adhesive coated on opposite sides and protected by release paper.

2 Claims, 2 Drawing Sheets

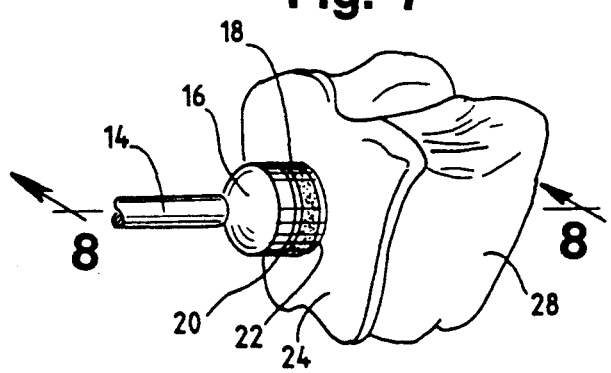
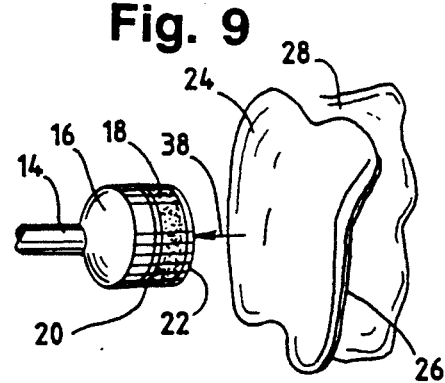
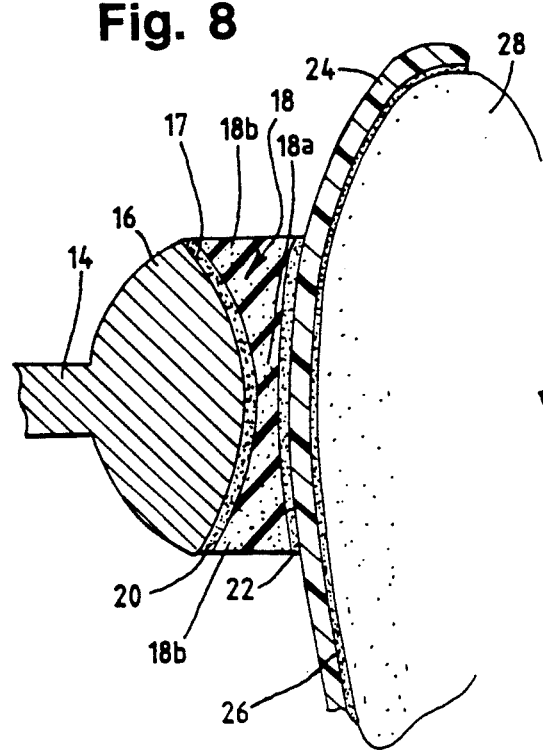
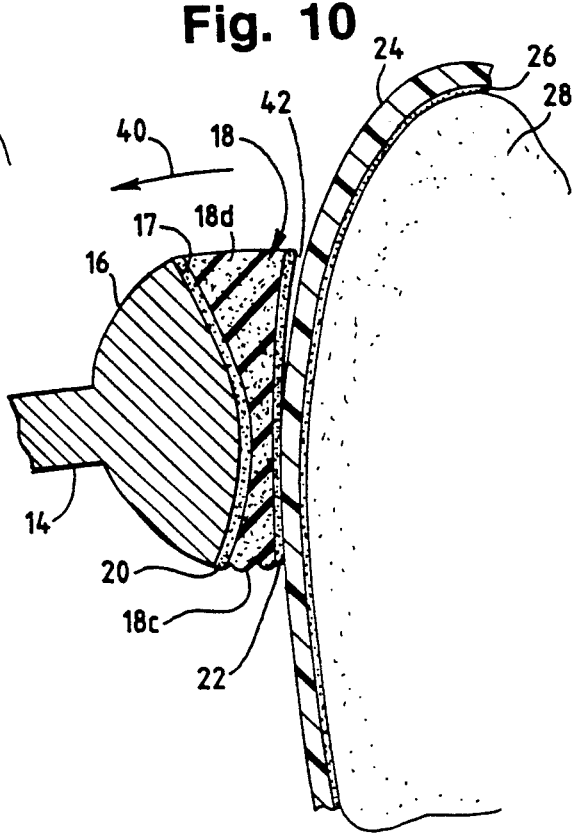
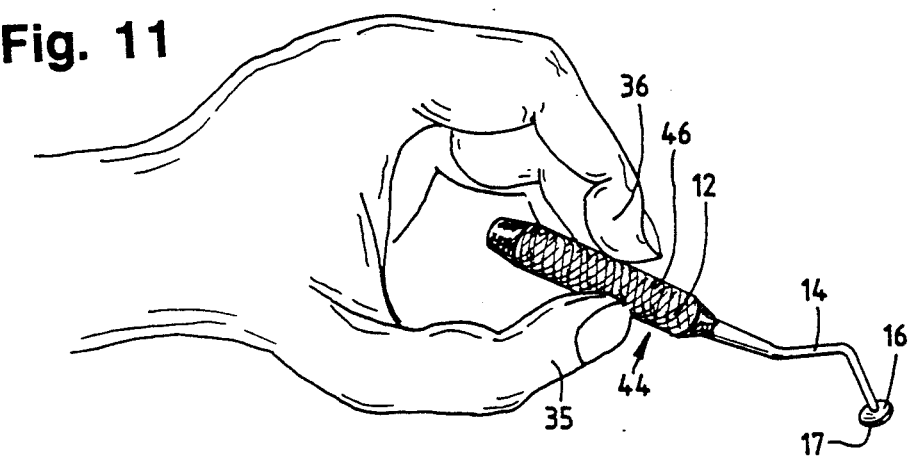

DENTAL PROSTHESIS PLACEMENT INSTRUMENT

RELATED APPLICATION

This application is a continuation-in-part of co-pending U.S. application, Ser. No. 07/655,797, filed Feb. 14, 1991, now abandon entitled "Dental Prosthesis Placement Instrument."

BACKGROUND OF THE INVENTION

This invention relates to a placement instrument for dental prosthetic devices. More particularly, it relates to an instrument for use in holding, matching, fitting and placing dental prosthetic devices in an efficient and time-conserving fashion.

In recent years, the use of dental prosthetic devices for both therapeutic and cosmetic purposes has greatly increased. Dental veneers, used to cover or cap a surface of a patient's disfigured or discolored tooth, are virtually unnoticeable when applied, and create a seemingly new tooth for the patient. Because the process of applying such a prosthesis is tedious and time consuming, however, dentists have been forced to work in ways which are both awkward and inefficient.

A dental veneer is applied to a patient's tooth by a dentist through a series of steps. The veneer, which conforms to the size, shape and color of the patient's tooth, is commonly a porcelain laminate selected from stock forms or manufactured by a laboratory from an impression of the patient's tooth.

Once the dentist has selected or received the correct veneer, and fitted and matched it to the tooth, the tooth and the veneer are readied for application. Typically, the dentist prepares both the tooth and veneer with an acid etching agent, applies a bonding agent to the etched surfaces, and puts the veneer in place. The bonding agent is then cured, typically by certain spectra of light which react with the bonding agent, after which the veneer is securely held in place by the bonding agent and the structural stability of the tooth. Then the dentist may file and polish the veneer.

The steps of selecting, sizing, fitting and fixation of the veneer to the tooth are time-consuming and cumbersome procedures which require that the veneer be mounted on the tooth several times. First, the dentist must be sure that the porcelain veneer material matches the color of the patient's teeth, a step which in itself may take several placements. In addition, since the dental veneer must conform exactly to the shape and size of the tooth which it will cover, the dentist must perform a number of trial fittings so as to insure a proper match. During these steps it is important to isolate the area where the veneer will be placed so not to contaminate the veneer and the tooth with foreign objects, such as saliva and food particles. Only after matching the size, fit and color of the veneer does the dentist place the veneer on the tooth for permanent application. This, as mentioned, is done with light-curable bonding agents which do not harden until exposed to certain spectra of light, thus allowing the dentist some additional time to move the veneer to its final location.

Currently, the dentist accomplishes each of these placement steps by using fingers or a dental instrument employing an adhesive or suction to hold the veneers. Unfortunately, both the manual and instrument-aided methods currently used can cause a number of problems for the dentist during the veneer fitting and application process.

When the manual method is used, if the fragile prosthesis slips and falls out of the dentist's fingers, it may be permanently damaged. Likewise, the veneer may break if the dentist applies too much pressure during placement. When the veneer is adjusted to assure a correct esthetic match and functional fit, the dentist is required to continually touch and move the veneer by hand, thus increasing the risk of contamination to the veneer and bonding agent. Finally, the dentist's fingers can shadow the light used to cure the bonding agent, thus causing an uneven bond and allowing microcavities to develop which adversely affect long-term adhesion.

The current instrument-aided methods available for applying dental veneers also cause problems. First, if the dentist uses a prior-art adhesive system to place the veneer, the adhesive between the instrument and the veneer frequently sticks to the veneer and subsequently must be removed by hand. Secondly, when the dentist permanently places the veneer using a prior-art adhesive system, subsequent withdrawal of the instrument may cause the adhesive to pull on the veneer and thus dislodge it.

Suction-type instruments have also been used for placing dental prostheses, but they require frequent removal and replacement of various nozzles and adaptors, thus increasing the risk of contamination. In addition, if the suction from such an instrument is not continuously and uniformly applied to the veneer, the latter may slip and drop during application, leading again to damage and contamination.

Accordingly, there is a need for an improved instrument to manipulate, fit and place a dental veneer on a patient's tooth. In attempting to fill this need, the present invention provides an improvement on prior-art adhesive systems, and in particular it provides a multi-adhesive system. While the use of adhesive materials for this purpose is not in itself novel, prior-art adhesive devices have not completely solved the problem of how to release a dental veneer without dislodging it after the adhesive has served its purpose of transporting the object to its final destination, and the problem of how to avoid leaving behind a residue of adhesive material when the job is finished.

FIGS. 1-7 of Seidler U.S. Pat. No. 4,073,530 disclose two embodiments of a small-object pick-up and manipulating device comprising a handle portion and a flexible metal pick-up portion which is apparently permanently coated with a pressure-sensitive adhesive layer. This adhesive layer is covered by a protective release paper which is removed before picking up a small object. After the small object is picked up and placed elsewhere, the pick-up portion is mechanically flexed and rotated to accomplish a rolling action which helps to separate the small object from the adhesive on the pick-up device. So long as the adhesive coating remains in place, however, this type of device is unsuitable for autoclaving and thus could not safely be reused in a dental environment. It also employs a broad metal tip which would cast too large a shadow during light-curing of the bonding agent.

FIGS. 8-10 of the Seidler patent disclose a somewhat different device employing a flexible pick-up tip formed of an elastomeric material which also has the capability of performing a rolling action when the small object is released. This elastomeric tip further complicates the problem of autoclaving in a dental environment, since most elastomeric materials do not withstand high temperatures.

In FIGS. 11 and 12 of Seidler it is suggested that a reservoir of adhesive material be provided at the tip of the instrument, instead of a thin layer. This embodiment is also unsuitable for autoclaving, because the adhesive material cannot withstand high temperatures either.

Brown U.S. Pat. No. 4,953,902 is specifically directed to the dental veneer applicator art, and like FIGS. 11 and 12 of Seidler above, it also employs a reservoir of adhesive material. Brown discloses an elongated handle having a plunger and cylinder forming a chamber to hold the adhesive material. Pressure on the handle allows the plunger to extrude a small portion of the adhesive material onto the veneer so that the instrument may pick up and place the veneer. The veneer is then secured to a tooth with a bonding agent. There is no discussion in Brown, however, of the problem of sterilization after use and how that problem is affected by the presence of left-over adhesive material in the chamber.

Nussbaum U.S. Pat. No. 4,834,654 discloses a dental prosthesis applicator comprising an elongated flat handle and a flexible adhesive strip. The adhesive strip is covered by a protective shield which is removed before use, thus exposing an adhesive surface. The prosthesis adheres to the adhesive surface, thereby allowing the dentist to place the prosthesis onto a tooth. A bonding agent between the prosthesis and the tooth is used for permanent placement. The handle and the adhesive strip are both quite broad, and must be made of transparent material to avoid shadowing the prosthesis during the curing process.

The problem of autoclaving is not mentioned in Nussbaum, and it may well be a disposable device since it is made of plastic. Reusable instruments are less expensive than disposable ones over the long run, however, and are also ecologically more desirable because they do not intensify the problem of waste disposal. In viewing the dental prosthesis during the matching and fitting steps, moreover, a dentist who uses the Nussbaum applicator is forced to look through the transparent material and therefore may not get a clear view, especially for the purposes of color matching.

Oliva U.S. Pat. No. 5,040,981 also discloses a device for manipulating dental prostheses. FIGS. 1, 2, and 4 disclose embodiments of the device comprising an elongated cylindrical handle terminating in an elongated tip support section and a concave tip. The tip sections are disposable items constructed from plastic or stiff paper. Although the tip surfaces are directly coated with adhesive, clean-up and sterilization of the tip is not mentioned. This limits the use of each tip section to only one patient. As previously noted, disposable devices are more expensive in the long run, and more damaging to the environment.

The Oliva device also presents a problem regarding the application of the adhesive. If the tips are not pre-coated, the adhesive must be applied by spraying, or by dipping the tip into an adhesive. This can be a messy and time-consuming job, and there is some danger that the reservoir of adhesive may become contaminated while it is left open during the procedure. Additionally, the tip section of the instrument may become contaminated when it is handled by the user's fingers while being placed onto the reusable handle.

The tips of the Oliva device are flat or concave, which is disadvantageous because not all veneers are the same shape, and because a flat or concave tip does not aid in the removal of the tip and the adhesive from the prosthesis.

SUMMARY OF THE INVENTION

Accordingly, it is an object of the present invention to provide a placement instrument which allows a dental prosthetic device to be quickly and efficiently sized, fitted and matched to a patient's tooth, and to be cleanly, easily, efficiently and accurately placed in a patient's mouth.

It is another object of the invention to provide a placement instrument which will allow a dental prosthetic device to be more fully exposed to the light needed to cure the bonding agent at the prosthesis/tooth connection, so to create a uniform and reliable bond.

It is yet another object of the invention to provide a placement instrument which will not leave a residue of adhesive material on the outer surfaces of the prosthetic device or the instrument, and will release the prosthesis completely after it is placed on the tooth, without disturbing the final placement of the prosthesis.

Still another object is to afford the dentist a clear view of the prosthesis during fitting and matching, and especially to avoid interposing any color-changing elements in the field of vision.

In accordance with these objectives, the present invention provides a placement instrument and a method of placement which employ a multiple adhesive system for manipulating and installing prosthetic devices. This system comprises the combination of a handpiece with a mounting surface at one end, and double-stick adhesive means comprising a pad with pressure-sensitive adhesive material on one side thereof adapted for releasable attachment to the prosthetic device and pressure-sensitive adhesive material on the opposite side thereof adapted for releasable attachment to the mounting surface. The mounting surface is preferably convex in shape.

When using the invention, the dentist first removes an upper release paper from the adhesive pad and places the mounting surface against the pad's exposed upper surface. The pad, now attached to the instrument, is then removed from a lower release paper and placed onto the exterior surface of the dental prosthesis. With the prosthesis thus connected to the pad and the instrument, the dentist locates the prosthesis inside the patient's mouth and begins the matching, fitting and placement steps. It is important to note that, because of the preciseness of the instrument, the dentist can achieve great accuracy in the matching and fitting steps, resulting ultimately in a better placement of the prosthesis.

After the dentist completes all the requisite fittings and matchings, the prosthesis is then coated with the bonding agent for final installation. Using the invention, the dentist places the coated prosthesis onto the area of intended application, and then exposes the bonding agent to the curing light. Due to the narrow profile of the instrument, minimal shadows are created, thus resulting in a uniform and reliable bond. Finally, with the prosthesis permanently in place, the dentist easily detaches both the instrument and the pad from the prosthesis by using a simple rolling action which takes advantage of the convex shape of the mounting surface. Subsequent clean-up and sterilization are very easy, due to the use of pressure-sensitive adhesive material which allows the adhesive pad to be completely removed from the prosthesis without disturbing its placement or leaving any adhesive residue behind.

After the instrument is withdrawn from the patient's mouth, the adhesive pad may be readily detached from the instrument, once again leaving behind no adhesive residue. The instrument may then be sterilized in an autoclave before re-use.

The above features, objects and advantages of the invention will become apparent from the following detailed description of an illustrative embodiment of the invention, in which reference is made to the accompanying drawings.

BRIEF DESCRIPTION OF THE DRAWINGS

FIG. 7 is a fragmentary perspective view of the same embodiment of the invention, depicting the enlarged, rounded tip of the placement instrument attached to the double-stick adhesive pad, the latter also attached to the dental veneer, and the veneer being placed onto the patient's tooth;

FIG. 8 is a cross-section, taken along line 8—8 of FIG. 7, depicting the three-way adhesive connections between the patient's tooth, the dental veneer, the double-stick adhesive pad, and the rounded tip of the placement instrument;

FIG. 9 is a fragmentary perspective view of the same embodiment of the invention, depicting the placement instrument being used to remove the double-stick adhesive pad from the dental veneer, leaving the latter attached to the patient's tooth;

FIG. 10 is a view similar to FIG. 8, but shows the initial stages of withdrawal of the adhesive pad and placement instrument from the veneer after final placement of the latter on the tooth; and FIG. 11 is a perspective view of an additional embodiment of the invention, depicting the placement instrument with a shortened handpiece.

In the various figures of the drawing, like parts are indicated by like reference characters.

DETAILED DESCRIPTION OF THE PREFERRED EMBODIMENT

Figure 1:
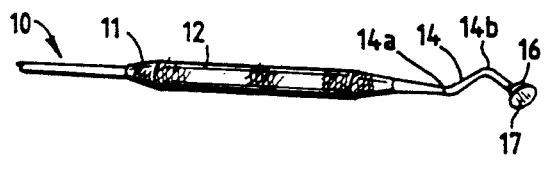
FIG. 1 is a perspective view of a preferred embodiment of the invention depicting a placement instrument which may be used to manipulate a dental prosthesis.
Figure 2:
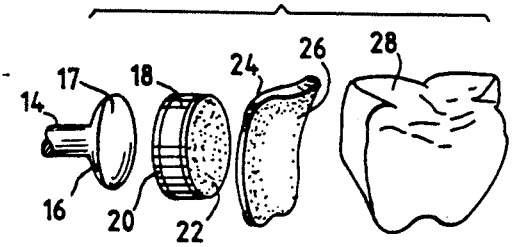
FIG. 2 is a fragmentary perspective view of the same embodiment, more clearly depicting the placement instrument with its enlarged tip and convexly rounded mounting surface, a double-stick adhesive pad, a dental veneer coated with a bonding agent, and a patient's tooth.

In accordance with this invention, a placement instrument generally designated 10 is employed in conjunction with a double-stick pressure-sensitive adhesive pad 18 to assist a dentist in the matching, fitting and placement of a dental prothesis 24. The placement instrument 10 comprises a handpiece with an elongated handle 11 having a knurled gripping section 12 and an angled, tapering terminal section 14. The terminal section 14 has a first intermediate bend 14a of approximately 20 to 30 degrees and a second intermediate bend 14b of approximately 60 to 75 degrees in order to facilitate intraoral access. The terminal section 14 terminates in an enlarged tip 16 formed with a convex, generally spherical mounting surface 17, preferably having a radius of curvature of about ⅛", at its distal end.

Releasable attachment of the instrument 10 to the dental veneer 24 is accomplished by the use of a double-stick pad 18 having one layer of pressure-sensitive adhesive material 20 applied to the top side of the pad and another such layer 22 applied to the bottom side. The pads 18 are pre-packaged with an upper release paper 30 covering the adhesive material 20 on the top of the pad and a lower release paper 32 covering the adhesive material 22 on the bottom of the pad. One example of the upper release paper is Rayven Polyester 50 gms., product No. RE 145, which is a polyester film with a silicon coating applied to the release side, manufactured by the Rayven Company of St. Paul, Minn. Examples of the lower release paper are product No. 68351700, further described as BL 50 mg. 13 Silox G9C/0, manufactured by the Akrosil Company of Menasha, Wis.; and product No. 1-65KG-165H, further described as a 60-pound, buff color, super calendared kraft glassine paper, coated on one side with elevated release coating 165H, which is manufactured by Daubert Coated Products, Inc. of Oak Brook, Ill.

The placement instrument 10 is constructed out of stainless steel or a similar heat-resistant material which may be sterilized in an autoclave before re-use. The double-stick pad 18, on the other hand, can be removed before autoclaving, and is therefore disposable rather than reusable. It is formed from a resiliently compressible plastic foam material which is porous enough to bond tightly to the adhesive materials 20 and 22 on both sides. Furthermore, the foam material of the double-stick pad 18 is strong enough not to tear when the release papers 30 and 32 are removed, and when the double-stick adhesive pad 18 is detached from the dental veneer 24 and placement tool 10. The porous nature of the foam pad 18 allows both adhesives 20 and 22 to adhere more strongly to the pad than to the placement instrument 10 or 24 veneer respectively, and therefore no residue of adhesive is left behind on the placement instrument or the veneer when the pad 18 is detached therefrom.

One example of the double-stick, pressure-sensitive adhesive pad 18 is FasTape TM 2132, coated on both sides by Avery Specialty Tape Division's I-406 pressure-sensitive adhesive. Both the pad and the adhesive are manufactured by the Avery Company of Painesville, Ohio.

An advantage of the invention is particularly evident in FIG. 8, which illustrates how the compressibility of the foam pad 18 enables it to deform and thus conform to the convexly curved outer surface of the veneer 24, and to the convexly curved mounting surface 17 of the enlarged tip 16. This compressibility makes for a more reliable adhesive connection than could be achieved by means of a less conformable adhesive-bearing surface.

The curvature of mounting surface 17 and the ability of the foam pad 18 to be compressed aid as well in the removal of the adhesive 22 from the prosthesis 24. Frequently, with the prior art, adhesive residues are left behind on the prosthesis when the instrument is removed. However, with the compressible foam pad 18 of the present invention, the user is able to roll the instrument when removing the pad 18 from the prosthesis 24, resulting in easier release of the pad from the prosthesis. It also has been empirically observed that the pad 18 more readily releases from the prosthesis 24 when used with a convexly curved mounting surface 17 as opposed to a flat mounting surface.

The bonding agent 26 which attaches the veneer 24 to the tooth 28 is stronger (after curing) than the adhesive material 22 which attaches the pad 18 to the veneer 24. This allows the dentist to detach the double-stick adhesive pad 18 from the veneer 24 without disrupting the final placement of the veneer on the patient's tooth 28 as well as without leaving any residue of the adhesive material 22 on the veneer 24. Until curing occurs, however, the bonding agent 26 must be weaker than the other two adhesive materials 20 and 22, so that the veneer 24 can be adjusted, relative to the tooth 28 by means of the placement instrument and adhesive pad 18, prior to curing of the bonding agent.

Examples of the bonding agent are the product Porcelite, manufactured by the Kerr Company of Romulus, Mich.; and the product Recover, manufactured by the Teledyne Getz Company of Elk Grove, Ill.

Figure 3:
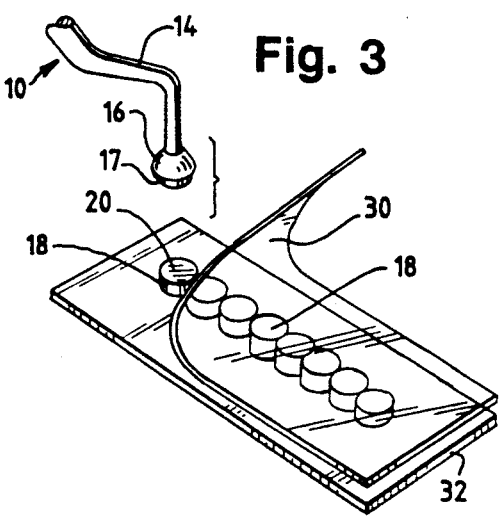
FIG. 3 is a fragmentary perspective view of the same embodiment, and also depicting a series of double-stick pads protected by upper and lower release papers, with the upper release paper partially removed, and a portion of the placement instrument just before the enlarged, rounded tip of the instrument attaches to one of the adhesive pads.

The operation of the invention will now be described. As shown in FIG. 3, the double-stick adhesive pad 18 is readied by removing upper release paper 30, thus exposing the upper adhesive material 20 to the convexly rounded mounting surface 17 of the tip 16 of the placement instrument 10. This surface 17 is then pressed against the top side of the double stick adhesive pad 18 and into adhesion therewith by means of the adhesive layer 20.

When the pad 18 is pressed into adhesion, it differentially compresses due to the convexly curved shape of mounting surface 17 of the enlarged tip 16. As seen in FIG. 8, the ⅛" radius of curvature defining the convex surface 17 forces the pad's center 18a to compress to between forty and sixty percent (40-60%) of its original thickness, while the pad's edges 18b remain roughly at their original thickness. This causes the pad 18 to "wrap" around the curved surface 17, which aids the user of the invention with the manipulation and placement of the prosthesis 24 because the adhesive forces between the pad 18 and the surface 17 are at least partly radial, and so that a dental prosthesis 24 can be adjusted laterally without the pad 18 tending to slip sidewardly away from the tip 16.

Figure 4:
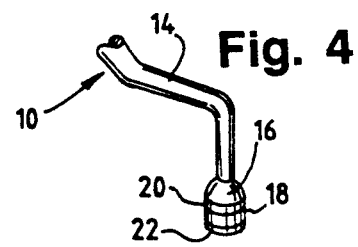
FIG. 4 is a fragmentary perspective view of the same embodiment of the invention, depicting a portion of the placement instrument with a double-stick adhesive pad attached thereto and the lower release paper removed.

With the tip 16 adhering to the adhesive layer 20, the instrument 10 may be used to lift the pad 18 from the lower release paper 32. The second adhesive material 22 is then exposed, FIG. 4, thus affording the dentist a means of picking up the dental veneer 24 for sizing, fitting and placement.

Figure 5:
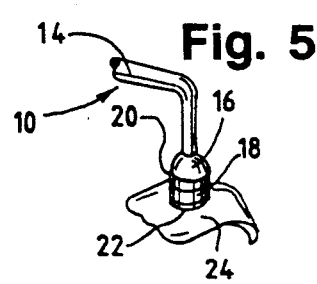
FIG. 5 is a fragmentary perspective view of the same embodiment of the invention, depicting a portion of the placement instrument attached to the double-stick adhesive pad and the latter also attached to a porcelain veneer.
Figure 6:
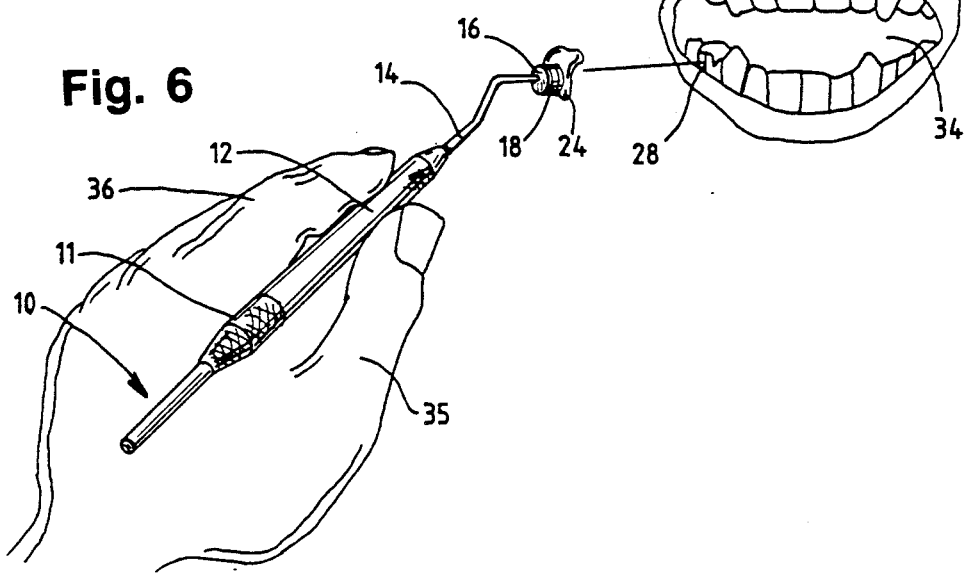
FIG. 6 is a perspective view of the same embodiment of the invention, depicting the placement instrument and double-stick adhesive pad in the process of carrying the veneer toward the patient's mouth for placement on a tooth.

As seen in FIG. 5, the dental veneer 24 is picked up by pressing the exposed adhesive material 22 onto the exterior convex surface of the dental veneer 24 (i.e. the surface which faces outwardly from the tooth 28 when the veneer is mounted thereon). The dentist then uses the placement instrument 10 and the adhesive pad 18 to size, fit and accurately place the veneer within the patient's mouth 34 as seen in FIG. 6. Using the thumb 35 and fingers 36 to hold the placement instrument 10 by the knurled grip 12, the dentist can achieve great control and accuracy in the placement of the dental veneer 24 on the tooth 28.

When the dentist places the veneer 24 for final application on the tooth 28, the instrument 10 and adhesive-coated pad 18 hold the veneer in place during curing of the bonding agent 26 which is located between the veneer and the tooth. With the veneer 24 still attached to the enlarged tip 16 of the placement instrument 10 by the double-stick adhesive pad 18, as seen in FIGS. 7 and 8, the bonding agent 26 is exposed to the curing radiation in the conventional manner. Because of its thin body 11, terminal section 14, and tip 16, the placement instrument 10 creates very small shadows when the radiant light source (not shown) is directed onto the veneer. This allows greater uniformity in the curing of the bonding agent, resulting in a more secure and solid bond.

After curing, the placement instrument 10 and double-stick adhesive pad 18 are detached from the veneer 24 as shown by the arrow 40 in FIG. 10. Because the adhesive strength of the cured bonding agent 26 is greater than that of the pad's adhesive materials 20 and 22, the instrument 10 and adhesive pad 18 separate from the veneer at the outer adhesive layer 22, leaving the veneer 24 permanently placed on the tooth 28. Subsequently, the pad 18 is stripped from the mounting surface 17 of instrument 10 and discarded, allowing the instrument 10 to be later autoclaved and reused. Both of the adhesive layers 20 and 22 cling preferentially to the pad 18, and thus do not leave behind any adhesive material 22 on the veneer 24 or any adhesive material 20 on the instrument surface 17. Most importantly, however, after curing of the bonding agent 26, the adhesive layer 22 releases without disturbing the permanent placement of the veneer 24.

The deformed foam pad 18 and the convex curvature of the mounting surface 17 play an important role in the removal of the pad 18 from the placed prosthesis 24. As seen in FIG. 10, the placement instrument is rotated in the manner illustrated by arrow 40 while at the same time it is pulled outwardly as indicated by arrow 38 of FIG. 9. The curved shape of the mounting surface 17 of the tip 16 enhances the resulting rolling action, and as a result, the pad is compressed at one side 18c where the instrument tip 16 rolls towards the veneer 24, and simultaneously is stretched at the other side 18d where the tip 16 rolls away from the veneer 24. The result of this differential stress is to exert maximum pulling force at location 42, causing the adhesive layer to separate from the veneer first at that location, as seen in FIG. 10. Subsequently, the separation 42 propagates quickly and cleanly across the face of the veneer 24, allowing the pad 18 to peel away from the veneer without tearing and without leaving any part of the pad or any residue of the adhesive 22 behind on the veneer, which would inconvenience both the dentist and the patient.

This rolling, peeling action, which is made possible by the choice of a resilient, compressible material for the pad 18, and a convexly rounded shape for the mounting surface 17, is similar to the rolling removal operation discussed above in connection with the prior art Seidler U.S. Pat. .No. 4,073,530; but here it is achieved less expensively and more conveniently by using the inherent compressibility of the disposable foam pad 18 instead of fabricating a flexible member out of metal, which is more expensive, or out of rubber or some other elastomeric material, which would preclude autoclaving. The elastomeric pad 18 of coursé is not autoclavable either, but the double-stick aspect thereof permits it to be removed from the handpiece 10 as well as from the veneer 24, thus permitting autoclaving of the handpiece.

An alternative embodiment of the invention is shown in FIG. 11, wherein instrument 44 corresponds operationally and functionally with the preferred embodiment of FIGS. 1–10, yet is shorter in length for use as a fingertip instrument. More particularly, instrument 44 comprises a handpiece with a fingertip handle 46 having a knurled gripping section 12 and angled tapering terminal section 14. The terminal section 14 has an enlarged tip 16, formed with a convex, generally spherical mounting surface 17, preferably having a radius of curvature of about ⅛", at its distal end. Like the preferred embodiment, the fingertip instrument 44 is constructed out of stainless steel or similar heat-resistant material which may be sterilized in an autoclave before re-use.

The handle 46 of the fingertip instrument 44 is a shortened version of the elongated handle 11 of the preferred embodiment, as shown in FIGS. 1 and 6, yet still provides the dentist with great control and accuracy in the placement of dental prostheses. The tapering terminal section 14, the enlarged tip 16 and convex mounting surface 17, as well as the methods for attaching a prosthesis and removing the double-stick adhesive pad 18, are all identical to those described above for the preferred embodiment. When using the fingertip instrument 44, the dentist holds it with the tips of the thumb 35 and forefingers 36 and then proceeds to manipulate and place dental prostheses as described above for the preferred embodiment.

It will now be appreciated that this invention provides a placement instrument which permits a dentist to hold, size, fit and match dental prostheses with greater ease; to efficiently and accurately manipulate and place such prostheses; to uniformly cure the necessary bonding agent; and to remove the adhesive without disturbing the placed prosthesis or leaving behind any adhesive on the prosthesis or the instrument.

While the principles of the invention have been described above in connection with certain specific embodiments, this description is intended only by way of example and not as a limitation on the scope of the invention, which is stated more broadly in the appended claims.

The invention claimed is:

1. A reusable prosthetic device placement instrument which employs a multiple adhesive system for manipulating prosthetic devices comprising:

a handpiece with a tip having a mounting surface at one end; and a double-stick adhesive member having a pad with pressure-sensitive adhesive material on one side thereof adapted for releasable attachment to a prosthetic device and pressure-sensitive adhesive material on a second side thereof adapted for releasable attachment to said mounting surface;

wherein said pad includes a resiliently compressible material to facilitate a rolling action upon detachment of said prosthetic device and wherein said mounting surface is substantially convex to enhance said rolling action.

2. A multiple adhesive system for manipulating prosthetic devices; comprising:

a reusable and autoclavable prosthetic device placement instrument including a hand piece with a surface at one end adapted to receive an adhesive means, said surface being substantially convex;

a double-stick means comprising a pad with pressure-sensitive adhesive material on one side thereof adapted for releasable attachment to a prosthetic device and pressure-sensitive adhesive material on the opposite thereof adapted for releasable attachment to said surface of said instrument; and a curable bonding agent adapted to hold the prosthetic device permanently in place;

both said adhesive materials being adhesively stronger than said bonding agent before curing, whereby to permit relocation of said prosthetic device, and adhesively weaker than said bonding agent after curing, whereby to avoid dislodging said prosthetic device.

* * * * *